United States Patent [19]
Barri et al.

[11] Patent Number: 5,434,328
[45] Date of Patent: Jul. 18, 1995

[54] RESTRUCTURING OF OLEFINS

[75] Inventors: Sami A. I. Barri, South Ascot; Rabaab Tahir, Hounslow; David W. Walker, Ashford, all of England

[73] Assignee: The British Petroleum Company p.l.c., London, England

[21] Appl. No.: 44,436

[22] Filed: Apr. 30, 1987

[30] Foreign Application Priority Data

May 27, 1986 [GB] United Kingdom ............... 8612815

[51] Int. Cl.⁶ .......................... C07C 5/23; C07C 5/27
[52] U.S. Cl. ..................................... 585/666; 585/671
[58] Field of Search ............................. 585/666, 671

[56] References Cited

U.S. PATENT DOCUMENTS

| | | | |
|---|---|---|---|
| 4,081,490 | 3/1978 | Plank et al. | |
| 4,324,940 | 4/1982 | Dessau | 585/666 |
| 4,587,375 | 5/1986 | Debras et al. | 585/671 |
| 4,753,720 | 6/1988 | Morrison | 585/666 |
| 4,814,543 | 3/1989 | Chen et al. | 585/739 |
| 5,157,194 | 10/1992 | Rahmim et al. | 585/671 |

FOREIGN PATENT DOCUMENTS

| | | |
|---|---|---|
| 87017 | 8/1983 | European Pat. Off. |
| 102467 | 3/1984 | European Pat. Off. |
| 150105 | 7/1985 | European Pat. Off. |
| 170003 | 2/1986 | European Pat. Off. |

OTHER PUBLICATIONS

Barrer, "Hydrothermal Chemistry of Zeolites", Academic Press, 1982, p. 24.

*Primary Examiner*—Asok Pal
*Attorney, Agent, or Firm*—Brooks Haidt Haffner & Delahunty

[57] ABSTRACT

This invention relates to a process for restructuring an olefinic feedstock rich in linear olefins into a product olefin of narrower composition which is richer in branched olefins than the starting feedstock. Such restructuring is achieved by contacting the feedstock with an unmodified or partially modified tectometallosilicate of the Theta-1 type at relatively low temperatures. The product olefins are valuable as petrochemical feedstock for producing polyolefins, alcohols, ethers and other oxygenates, surfactants, alkyl aromatics and oligomers useful as gasoline blending components.

10 Claims, No Drawings

RESTRUCTURING OF OLEFINS

The present invention relates to a process for restructuring olefins especially linear olefins in the presence of tectometallosilicates of the Theta-1 (the so-called "TON") type.

Zeolites are well known natural and synthetic compounds. Many of them have been demonstrated to have catalytic properties for various types of hydrocarbon conversion and related reactions. Zeolites can be defined as ordered porous crystalline aluminosilicate having a framework structure consisting of a rigid regular three dimensional network of $SiO_4$ and $AlO_4$ tetrahedra in which the tetrahedra are cross-linked by sharing the oxygen atoms and which are sufficiently open to accommodate at least water molecules. Such structures generally contain a regular array of small voids interconnected by channels or pores. The dimensions of the voids and channels can range from those of water to those of quite large molecules. For a given framework structure, the dimensions of the voids and channels are limited to a small number of values, which can vary from structure to structure. Thus these structures are capable of sorbing molecules of certain dimensions while rejecting those of dimensions larger than a critical value which varies with structure type. This has led to zeolites being used as molecular sieves. Zeolites belong to a class of materials that can be termed tectoaluminosilicates which comprise (in addition to zeolites) feldspars and feldspathoids. All oxygen atoms forming the tetrahedra are shared, thus the ratio of total aluminium and silicon atoms to oxygen atoms is 1:2.

Zeolites are best characterised according to framework structure type, i.e. on the topology of the framework, irrespective of composition, distribution of different tetrahedral atoms, cell dimensions and symmetry. A code consisting of three capital letters has been adopted for each known structure type following the recommendations by IUPAC on zeolite nomenclature ("Chemical Nomenclature, and Formulation of compositions, of Synthetic and Natural Zeolites", IUPAC yellow booklet, 1978) and a compilation of 38 known zeolite structure types has been published by The Structure Commission of the International Zeolite Association ("Atlas of Zeolite Structure Types", by Meier, W. M. and Olsen, D. H. (1978), distributed by Polycrystal Book Service, Pittsburgh, Pa., USA). In addition to the groups classified by known structure type, there is a further group of crystalline zeolite materials whose X-ray diffraction patterns, sorption, ion-exchange and related properties indicate that they do not have known structure types but appear to have new structure types. These new class of zeolites have unidimensional, non-intersecting channels with ten-membered ring openings up to 6 Å in diameter and are classed as the "TON-type" under the three letter coding of structure type. Theta-1 is an example of such a novel porous crystalline aluminosilicate and is described in our published European patent specification No. 0057049.

There are several prior art publications which indicate that $C_2$–$C_{10}$ olefinic feedstocks can be restructured over a special zeolite to form primarily $C_4$–$C_7$ olefins. One such publication is EP-A-0026041 which describes the use of an MFI (ZSM-5) type zeolite for this purpose. However, when using MFI type zeolites the selectivity towards the restructured olefins is relatively low due to the formation of undesirably high amounts of alkane by-products in such reactions.

Zeolites of the Theta-1 and ZSM-23 type are expected to have similar catalytic properties to MFI-type aluminosilicate because of very similar physiochemical properties. MFI-, Theta-1 and ZSM-23 type aluminosilicate can be prepared with very similar $SiO_2/Al_2O_3$ ratios and with near identical shape-selective sorption characteristics. For example, they both sorb and desorb xylenes. They can be prepared from very similar starting gels (including the same type of template such as an alkanolamine) subjected to identical digestion parameters, see for example our European Patent Specification No. 0057049. Thus it could be reasonably expected that subjecting a mixture of olefins over an un-modified hydrogen-form of Theta-1 or ZSM-23 type aluminosilicate to a restructuring reaction should lead to a product having a relatively high proportion of alkanes in addition to the restructured olefins if exposed to conditions under which an unmodified hydrogen-form of the MFI type aluminosilicate leads to formation of a similar product mixture.

Surprisingly, it has now been found that if a catalyst containing an unmodified hydrogen form of Theta-1 or ZSM-23 type aluminosilicate is used for restructuring one or more olefins, the process is highly selective in that the product mixture has a high proportion of restructured olefins and a relatively low proportion of alkanes.

Accordingly, the present invention is a process for restructuring a $C_2$–$C_{10}$ olefinic feedstock rich in linear olefins, said process comprising bringing the olefinic feedstock in the fluid phase into contact with a tectometallosilicate in its unmodified or partially modified H-form at an elevated temperature characterised in that the tectometallosilicate in its calcined, organic free hydrogen form has the following composition in terms of the mole ratios of the oxides:

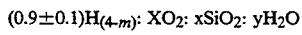

$$(0.9 \pm 0.1) H_{(4-m)}: XO_2: xSiO_2: yH_2O$$

wherein H is a proton, X is one or more of the metals selected from Al, Ga, Zn, Fe, Cr and B, m is the valency of the metal X in the metal oxide $XO_2$, x is at least 10, y/x is from 0 to 5 and the tectometallosilicate in its unmodified or partially modified H-form has an X-ray diffraction pattern substantially as set forth in Table A (Theta-1) or Table B (ZSM-23) of this specification.

By the term "tectometallosilicate in its unmodified or partially modified H-form" is meant here and throughout this specification that the as synthesised tectometallosilicate when using an organic nitrogen containing base as template has been calcined at a temperature of at least 100° C. prior to use. The as synthesised tectometallosilicates prepared using organic bases contain organics and therefore have to be calcined in air to remove the organic materials. The calcination is suitably carried out at a temperature from 200°–600° C., preferably from 300°–550° C. Calcination in this temperature range can be carried out on the as synthesised zeolite and/or on the alkali metal free form thereof. The temperature and duration of the calcination would depend upon whether a partially modified or an unmodified H-form of the zeolite is desired.

For instance, calcination at 300°–400° C. for a duration of 16 hours should result in a partially modified H-form of the zeolite irrespective of the template used. However, if the calcination is carried out at 500°–600°

C. for a duration of 16 hours, the resultant product should be considered the unmodified H-form of the zeolite. Where the as synthesised catalyst is produced using ammonia as the template, it may not be necessary to calcine the product prior to use. However, the as synthesised form produced using ammonia as the template can also be modified either as such or after conversion thereof to the H-form by stirring the tectometallosilicate in an organic compound such as diethanolamine or in an aqueous solution of an organic compound, e.g. an alkanolamine at a temperature e.g. from 80°–120° C. Thereafter, the tectometallosilicate can be dried and calcined at a temperature from 200°–600° C., preferably from 300°–550° C. as mentioned previously. This is another method of producing partially modified tectometallosilicates for use in the present invention.

The $H_2O$ content "y" of the tectometallosilicate is the water of hydration and will depend, within the ratios set out above, upon the conditions under which it is dried, calcined, subjected to further aqueous treatments or combinations thereof after synthesis. The $H_2O$ content "y" does not include water which may be notionally present when the cation is hydrogen.

The cation in the tectometallosilicate is essentially H though very small amounts of other cations such as ammonium, alkali metal cations, alkaline earth metal cations, organic nitrogen containing cations, aluminium cation, and mixtures thereof which have not been completely removed, may also be present.

The cations present in the tectometallosilicate may be replaced using conventional ion exchange techniques either wholly or partially by other cations e.g. hydrogen ions or metal cations.

The tectometallosilicate used herein may be produced in its unmodified or partially modified hydrogen-form by known methods such as exchange with hydrogen ions or with ammonium cations followed by one or more calcinations or a combination of the two followed by one or more calcination stages, if the tectometallosilicate still contained ammonium ions.

The metal X in the metal oxide $XO_2$ is preferably Al, Ga, Zn, Fe, B or Cr. In the tectometallosilicate the molar ratio of silica to metal X is preferably from 10:1 to 200:1.

Where the tectometallosilicates according to the present invention is Theta-1, it has in its organic-free hydrogen form an X-ray diffraction pattern shown in Table A below. The specific values in the Table were determined using copper K-alpha radiation and a computer step scan.

The peak heights, I, and their position as a function of 2-theta, where theta is the Bragg angle, were read from the spectrometer output. From this output the relative intensities 100 $\times I/I_o$, where $I_o$ is the intensity of the strongest peak, and d the interplanar spacing in A, corresponding to the recorded peaks were calculated.

It will be understood by those skilled in the art that the X-ray diffraction pattern of tectometallosilicates may vary in the values of $I/I_o$ and the d-spacing depending for example upon whether the sample being examined is calcined or uncalcined, upon the temperature of calcination, upon the nature of the cation present in the tectometallosilicate, the mole ratio of silica to metal oxide, and the particle size of the tectometallosilicate.

The tectometallosilicate is suitably produced by mixing a source of silica, a source of alumina, a source of alkali metal(s), water and an organic or inorganic nitrogen containing base until a homogeneous gel is formed and crystallising the gel at a temperature above 70° C.

TABLE A

| 2-theta (degrees) | d-spacing (Angstroms) | Relative Intensity 100 × $I/I_o$ |
|---|---|---|
| 8.06 ± 0.2 | 11.25–10.70 | 50 to 100 |
| 10.06 ± 0.2 | 9.01–8.63 | 5 to 30 |
| 12.69 ± 0.2 | 7.09–6.87 | 10 to 30 |
| 16.28 ± 0.2 | 5.51–5.38 | 5 to 15 |
| 19.40 ± 0.2 | 4.62–4.53 | 5 to 15 |
| 20.26 ± 0.2 | 4.43–4.34 | 50 to 100 |
| 24.11 ± 0.2 | 3.72–3.66 | 50 to 100 |
| 24.52 ± 0.2 | 3.66–3.60 | 30 to 90 |
| 25.65 ± 0.2 | 3.50–3.45 | 15 to 45 | scanned up to 2 theta = 32

TABLE B

| 2-theta (degrees) | d-spacing (Angstroms) | Relative Intensity 100 × $I/I_o$ |
|---|---|---|
| 7.94 ± 0.2 | 11.41–10.85 | 50 to 100 |
| 8.24 ± 0.2 | 10.99–10.47 | 50 to 100 |
| 8.95 ± 0.2 | 10.10–9.66 | 20 to 50 |
| 11.44 ± 0.2 | 7.86–7.59 | 20 to 50 |
| 14.68 ± 0.2 | 6.11–5.95 | 5 to 10 |
| 15.90 ± 0.2 | 5.64–5.50 | 5 to 10 |
| 16.41 ± 0.2 | 5.75–5.39 | 5 to 10 |
| 18.28 ± 0.2 | 4.90–4.80 | 5 to 20 |
| 19.78 ± 0.2 | 4.53–4.44 | 50 to 100 |
| 20.16 ± 0.2 | 4.44–4.36 | 10 to 30 |
| 21.04 ± 0.2 | 4.26–4.18 | 50 to 100 |
| 22.98 ± 0.2 | 3.90–3.83 | 70 to 100 |
| 24.17 ± 0.2 | 3.71–3.65 | 50 to 100 |
| 24.82 ± 0.2 | 3.61–3.56 | 20 to 70 |
| 25.32 ± 0.2 | 3.54–3.49 | 20 to 60 |
| 26.15 ± 0.2 | 3.43–3.38 | 20 to 60 | scanned up to 2 theta = 32

In both Tables A and B peaks having a relative intensity (100×$I/I_o$) below 5 and/or a 2 theta value greater than 27 have been omitted.

The tectometallosilicates used in the present invention may be bound in a suitable binding material using methods and binding materials well known in the art. Examples of binders that may be suitably used include silica, alumina and clays such as kaolin and meta-kaolin. The catalyst composition may be subjected to further activation treatments e.g. thermochemically, which is heating for instance in steam or in an inert gas e.g. nitrogen in an oxidative environment such as dry air or molecular oxygen, or in a reductive environment such as dry hydrogen prior to contact with the olefinic feedstock. Such further treatments may be carried out during one or more of the catalyst preparation stages.

It is preferable to carry out the activation treatment in air or nitrogen. For instance the treatment temperature is suitably from 300°–600° C., preferably from 350°–550° C. The treatment pressure may vary from 100 to 5000 KPa but is preferably from 100 to 2000 MPa. The treatment may be carried out over a duration of 5 minutes to 200 hours, preferably from 1–20 hours.

It will be appreciated by those skilled in the art that the conditions specified for any of the aforementioned treatments will be interdependent. Increasing the severity of one or more of the parameters may allow a reduction in the severity of the other relevant treatment.

The term "restructuring" or "restructured" as used herein and throughout the specification is meant to include isomerisation and/or rearrangement of an olefinic feedstock having a wide product composition e.g.

$C_2$–$C_{10}$ olefins which is rich in linear olefins into an olefinic product of a narrower composition e.g. $C_4$–$C_{10}$ which has a higher proportion of branched chain olefins than the starting olefinic feedstock. Thus, for instance n-olefins are converted into iso-olefins.

The olefinic feedstock which may be restructured to the branched chain olefinic compounds by contact with the unmodified tectometallosilicates herein defined are suitably $C_4$–$C_{10}$ linear olefinic hydrocarbons, preferably $C_4$–$C_6$ linear olefins. The olefinic feed is preferably diluted with a gas inert under the reaction conditions such as e.g. nitrogen or $C_1$–$C_{10}$ alkanes. It is a feature of the present invention that when an olefinic feedstock, such as e.g. n-butenes, mixed with an inert diluent is subjected to a restructuring reaction as in the present invention, the proportion of the restructured olefins in the product mix is further improved.

The restructuring reaction is suitably carried out from 200°–550° C., preferably from 200°–500° C., the precise temperature within this range depending upon other variables such as type of olefinic feedstock and the other reaction conditions. It is preferable that the temperature of the catalyst is raised to the reaction temperature in the presence of the olefinic feedstock whether or not it contains the diluent.

The restructuring reaction is suitably carried out at a pressure from 100 to 1000 KPa, preferably from 100 to 300 MPa.

Where an olefinic feedstock is mixed with an inert diluent, the diluent is suitably present in an amount of at least 50% v/v, preferably from 60–90% v/v of the total mixed feed.

The weight hourly space velocity of the olefinic feedstock over the tectometallosilicate is suitably in the range of 1–100 WHSV, preferably 2–30 WHSV.

The products of the restructuring reaction are principally olefinic hydrocarbons which are rich in branched chain olefins e.g. iso-butenes and iso-pentenes. The restructuring reaction is efficient and selective in that by-products such as methane and alkanes are formed only in very small amounts.

The products from the reaction can be separated according to their properties e.g. melting point, boiling point, polarity etc, or to their molecular dimensions. Methods such as molecular sieving, distillation, selective adsorption can be used to achieve separation.

The product rich in branched chain olefins are valuable as a petrochemical feedstock for producing polyolefins, alcohols, ethers and other oxygenates, surfactants and alkylaromatics, and as a feedstock for producing olefin oligomers which are useful as gasoline blending components.

The present invention is further illustrated with reference to the following Examples.

EXAMPLES—Using TON and ZSM-23 Zeolites

A. Catalyst Preparation (1) Theta-1 (TON)

Four samples of Theta-1 were used for the catalyst tests, with sample codes TON-A, TON-B, TON-C and TON-D respectively. The zeolites were prepared as follows.

Sample TON-A

Sodium aluminate (41% w/w $Al_2O_3$, 29.6% w/w, $Na_2O$, 29.4% w/w $H_2O$) (19.5 g) and sodium hydroxide (10.1 g) were dissolved in distilled water (156 g). To this solution was added ammonia solution (SG 0.91) (910 g). Colloidal silica (780 g) (DuPont Ludox AS40 40% w/w $SiO_2$) was added to this solution with stirring until a homogeneous gel was obtained. The gel was loaded into a rocking autoclave and heated at 175° C. for ca 20 hours. The autoclave was allowed to cool, the resultant slurry was filtered and the solid washed thoroughly with distilled water and then dried at 120° C. The product was analysed by X-ray diffraction and found to be Theta-1 with a trace of cristobalite. The Si:Al atomic ratio of the product determined by X-ray fluorescence spectroscopy was 30:1.

Sample TON-B

The zeolite was prepared in an identical manner to that of TON-A above, except that the reagent weights were as follows:

Sodium aluminate 23.1 g
Sodium hydroxide 5.7 g
Water 150 g
Ludox AS40 750 g
Ammonia solution (SG 0.91) 870 g The product was filtered, washed and dried in the same manner as for sample TON-A. The product was analysed by X-ray diffraction and found to be Theta-1 with a trace of cristobalite. the Si:Al (atomic ratio) of the product was determined by X-ray fluoroescence spectroscopy to be 26:1.

Sample TON-C

Sodium aluminate (41% w/w $Al_2O_3$, 29.6% w/w $Na_2O$, 29.4% w/w $H_2O$) (14.0 g) and sodium hydroxide (6.69 g) were dissolved in distilled water (140 g). Methanolamine (DEA, 180 g) was added and the mixture thoroughly stirred. Distilled water (354 g) was added with stirring, followed by addition of colloidal silica (497 g) (Dupont Ludox AS40 40% w/w $SiO_2$) to the mixture which was then well stirred to give a homogeneous gel. The gel was equally divided into stainless steel bottles (capacity ca 200 mls each). These were rotated for 28 hours at 175° C. after which the product was filtered, washed well with distilled water and dried in an oven at 100° C.

The products were analysed by X-ray diffraction and were found to be Theta-1 with a trace amount of amorphous material. The Si:Al (atomic ratio) of the product was determined by X-ray fluorescence to be 37:1.

The product was next refluxed with aqueous ammonium nitrate solution (10 g/200 ml) (1M, 2×1 hr), filtered hot, washed well with distilled water and dried in an oven at 100° C. Prior to testing the same was calcined at 325° C. or 500° C. in air as indicated in Table 7. 5 ml (2.0 g) of the catalyst were pressed at 7 tonnes, pelleted to pass 8 mesh but not 16 mesh (BSS), packed into a silica reactor and activated overnight in air at 350° C. in situ. The system was flushed through with nitrogen and the temperature was increased to 400° C. under nitrogen.

Sample TON-D

Sodium aluminate (15.0 g) and sodium hydroxide (7.80 g) were dissolved in distilled water (120 g). Aqueous ammonia solution (700 g) (SG 0.91) was added and mixed thoroughly. Colloidal silica (600 g) was then added slowly with stirring to give a homogeneous gel. The gel was loaded into a rocking autoclave and heated at 175° C. for 20–25 hours. The autoclave was allowed to cool and the product was filtered, washed well with distilled water and dried in an oven at 100° C. The X-ray diffraction analysis showed a good sample containing more than 90% of Theta-1 in the product.

The product was refluxed with ammonium nitrate (10 g/200 ml) solution (1M, 2×1 hr) and calcined in air at 500° C. overnight. The H-form of TON-D so formed was refluxed with a 1:1 by volume mixture of diethanolamine and water (1.5 hr reflux). The weight ratio of TON-D to the DEA/H$_2$O mixture being 1:10. Following the reflux, the solid was filtered hot, washed well with distilled water and dried in an oven at 100° C.

5 ml (2.0 g) of the catalyst were pressed at 7 tonnes, pelleted to pass 8 mesh but not 16 mesh (BSS), packed into a silica reactor and calcined overnight in air. The zeolite was calcined at temperatures of 360° C. or 380° C. as shown in Table 7. The system was flushed through with nitrogen, and the temperature was increased to 400° C. in nitrogen.

(2) ZSM-23

Sodium aluminate (41% w/w Al$_2$O$_3$, 29.6% w/w Na$_2$O, 29.4% w/w H$_2$O) (3.0 g) and sodium hydroxide (1.5 g) were dissolved in distilled water (150 g). To this solution was added diisopropanolamine (60 g) and the mixture thoroughly mixed. Colloidal silica (150 g) (DuPont Ludox AS40 40% w/w SiO$_2$) was added to the mixture and then well stirred to give a homogeneous gel. The gel was split into three equal portions and put into three stainless steel bombs (capacity ca 200 cm$^3$ each). The bombs were sealed and heated at 180° C. A bomb each was taken out after 16, 24 and 40 hours of heating respectively. The first two bombs gave products that were amorphous. The bomb removed after 40 hours heating gave a product which when filtered, washed and dried was essentially ZSM-23 as determined by X-ray diffraction.

(3) MFI (ZSM-5)

Two samples of MFI with sample codes MFI-A and MFI-B respectively were used for the catalyst tests. The zeolites were prepared as follows.

MFI-A

Sodium aluminate (115 g) (41% w/w Al$_2$O$_3$, 29.6% w/w Na$_2$O, 29.4% w/w H$_2$O) and sodium hydroxide (34.1 g) were dissolved in distilled water (1520 g). This solution will be referred to as solution X. Ammonia solution (SG 0.91, 164 g) was added to colloidal silica (1765 g) (Ludox AS40). This solution will be referred to as solution Y. Solution Y was slowly added to solution X with constant stirring until a homogeneous gel was obtained. The gel was then transferred to a 1 gallon Parr autoclave and heated to 175° C. for 72 hours. The gel was stirred during the heating. After heating the autoclave and its contents were allowed to cool, before the contents were removed, filtered, thoroughly washed and dried.

The product of the synthesis was determined to be essentially MFI (ZSM-5) by X-ray diffraction. The Si:Al (atomic ratio) of the zeolite was determined by X-ray fluorescence to be 11.5:1.

MFI-B

Sodium aluminate (3.72 g) (41% w/w Al$_2$O$_3$, 29.6% w/w Na$_2$O, 29.4% w/w H$_2$O) and sodium hydroxide (2.63 g) were dissolved in distilled water (50 g). To this solution was added tetrapropylammonium hydroxide solution (66.6 g) (20% w/w in water). To the resulting solution colloidal silica (116.7 g) (Ludox AS40) was added with constant stirring to give a homogeneous gel. The gel was split into two aliquots and transferred to two stainless steel bombs (capacity ca 200 cm$^3$ each). The bombs were heated in an oven at 170° C. for ca 64 hours. The bombs were rotated in the oven during the heating period. After the heating period the bombs were allowed to cool and the contents removed, filtered, washed thoroughly and dried at 120° C.

The product of the synthesis was determined by X-ray diffraction to be essentially MFI (ZSM-5). The Si:Al atomic ratio of the product was determined by X-ray fluorescence spectroscopy to be 22:1.

The zeolites TON-A, TON-B, ZSM-23, MFI-A and MFI-B when synthesised as described above need to be converted to the unmodified or partially modified H-form before they are used for catalysis. The general procedure for converting the zeolites to the unmodified H-form is well known and was carried out in the following manner for the zeolite samples whose preparation has been described above.

1) The as-synthesised zeolites ZSM-23 and MFI-B were calcined in air as described below to remove organic templates used during the zeolite synthesis from the zeolite pores.

For the Theta-1 synthesis described (i.e. TON-A and TON-B) and for the MFI synthesis (MFI-A) no calcination step was necessary because no organic templates were used. For zeolite ZSM-23, which was prepared in the presence of diisopropanolamine, the as-synthesised zeolite was calcined in the following manner.

A sample of the zeolite was put in a tubular reactor and heated at 2° C./min to 200° C. and held at 200° C. for 1 hour. The temperature was then raised at 2° C./min to 600° C. and held at this temperature for 48 hours. The zeolite was allowed to cool down naturally to room temperature.

For zeolite MFI-B, which was synthesised in the presence of tetrapropylammonium hydroxide, the following calcination was carried out. A shallow silica tray was filled with a sample of the zeolite to a depth not greater than 3 mm. The tray was put in an electrically heated muffle furnace and calcined at 550° C. for 15 hours in a flow of air. After the heat treatment the zeolite was allowed to cool down naturally to room temperature.

2) The as-synthesised zeolites (for TON-A, TON-B and MFI-A) and the calcined zeolites (for ZSM-23 and MFI-B) were converted to their respective ammonium exchanged forms by the following procedure. The zeolites were each heated under reflux in an aqueous solution of one molar ammonium salt (e.g. either ammonium chloride or ammonium nitrate) for 1 hour. Approximately 10 cm$^3$ solution of the ammonium salt was used per gram of zeolite. After this treatment the zeolite slurry was filtered, and the zeolite washed thoroughly with distilled water. The zeolite was treated for a second time with fresh ammonium ion solution in an identical manner to the first. The zeolite slurry after the second treatment was again filtered, washed and the zeolite dried at ca 120° C. in an oven.

3) The ammonium form of the zeolite powders were granulated to a mesh size of 8–16 BSS by the following technique. Each zeolite was pelleted in a die (internal diameter 20 mm) in a press with an applied pressure of typically 1 to 5 tonnes. The pellets were then crushed and sieved to pass 8 but not 16 mesh BSS.

Samples of the sieved granulated zeolites were then tested for olefin restructuring in a manner described below. The weight of zeolite used for the catalyst tests varied from 0.5 g to 2.0 g. The weight used for a specific test is given in the Tables of Examples below:

B. Catalyst Testing

All catalysis were tested in a silica tubular reactor (internal diameter ca 10 mm) which was heated electrically. The feed used was 1-butene (99.9% w/w purity) at atmospheric pressure. Nitrogen, when used as a diluent, and air for calcination treatments were both greater than 99% w/w purity. All gases were dried before being fed to the reactor, by passing the gases through traps containing calcium chloride and phosphorous pentoxide.

Weighed samples of the granulated forms of the ammonium exchanged zeolites prepared as described in the previous section were loaded into the reactor prior to testing. The catalysis were then converted to the active hydrogen forms by decomposing the ammonium form by heating to an elevated temperature (typically 400°-600° C.) in a flow of either air or nitrogen. The exact activation procedure for each zeolite tested is given in the Tables of the Examples below.

Reactions were carried out for each catalyst over a range of temperatures. The general procedure to test a catalyst at a given temperature was as follows:

After the zeolite had been converted to the hydrogen form as described above, the zeolite was allowed to cool to the first reaction temperature in a flow of nitrogen. The 1-butene feed was then introduced into the nitrogen at the desired concentration for a diluted feed test. Alternatively, for pure feeds, the nitrogen flow was stopped when the 1-butene feed was introduced to the reactor.

The 1-butene flow was maintained for a definite period of time (typically 30-60 minutes) over the zeolite. The majority of the reaction products with carbon number greater or equal to 5 were collected in a cooled trap at the reactor exit. The majority of the hydrocarbons with a carbon number of less than 5 remained in the gas phase. The gas phase hydrocarbons were analysed by conventional gas chromatography techniques. Any liquid products produced during a run were collected in the trap and weighed after the run.

To test the zeolite at another reaction temperature, the zeolite was heated to the desired temperature in a flow of nitrogen. When the desired temperature was reached, the reaction run was carried out using the required 1-butene feed in exactly the same manner as described above.

A zeolite could optionally be calcined in air after a series of runs in order to remove carbonaceous residues on the zeolite. The conditions for the regeneration are stated in the Tables of Examples below where appropriate.

The performance of each zeolite for each reaction was assessed by calculating feed conversions and selectivities for the formation of specific products. The terms used in the Tables of Examples are defined below.

$$\text{1-butene conversion (mole \%)} = \frac{\text{moles 1-butene fed} - \text{moles 1-butene recovered}}{\text{moles 1-butene fed}} \times 100$$

$$\text{Selectivity for the formation of product X based on 1-butene fed (mole \%)} = \frac{\text{moles of product X recovered}}{\text{moles 1-butene fed} - \text{moles 1-butene recovered}} \times 100$$

$$\text{n-butene conversion (mole \%)} = \frac{\text{moles n-butene fed} - \text{moles n-butene recovered}}{\text{moles n-butene fed}} \times 100$$

$$\text{Selectivity for the formation of product X based on n-butenes fed (mole \%)} = \frac{\text{moles of product X recovered}}{\text{moles n-butene fed} - \text{moles n-butene recovered}} \times 100$$

-continued $$\text{Space velocity WHSV} = \frac{\text{weight of alkene (g) fed in 1 hour}}{\text{weight of catalyst (g)}}$$

In some of the Tables of Examples, the results have been quoted in both terms of 1-butene conversions and n-butene conversions. This is because 2-butenes produced from the reaction of 1-butene can be recycled and can be regarded as unreacted n-butene feed.

In the Tables, for conciseness, the products are referred to as follows:

$C_{1-3}$: methane, ethane, propane
$C_2=$: ethylene
$C_3=$: propylene
$2C_4=$: trans-2-butene + cis-2-butene
$iC_4=$: isobutene
$C_4$: isobutane + butane
$C_{5+}$: hydrocarbons with carbon number greater than or equal to 5
$C_{1-4}$: methane, ethane, ethylene, propane, propylene, butane, isobutane (unless stated otherwise)

C. Examples of Catalysis Tests

Examples of the catalysis tested using MFI zeolites and Theta-1 (TON) are presented in Tables 1-7 (inclusive) below. For each catalyst tested details of the reaction conditions and catalyst pretreatments are also given.

The olefin restructuring performances of MFI and TON, which have very similar Si:Al ratios, using a diluted 1-butene feed are presented in Table 1 below. It will be evident that TON is more than three times as selective for isobutene formation based on 1-butene fed than MFI (Table 1a) at 377-379° C. TON is also less selective for the less desirable lower hydrocarbon formation (i.e. with carbon numbers less than or equal to 3). The results are also compared in terms of n-butene fed in Table 1 (b). It is also evident that the $C_5$-hydrocarbons produced over TON are mainly alkenes (Table 1 (c)). These alkenes are known to be rich in isoalkenes which are valuable products. For reactions over MFI the $C_5$-hydrocarbons contained significant amounts of alkanes which are less valuable products.

The performance of MFI and TON which have different Si:Al ratios for olefin restructuring using a pure 1-butene feed are also presented in Table 2. It is evident that whilst both zeolites give relatively low selectivities (i.e. less than 10 mole %) for isobutene formation (Table 2 (a)) at 273°-278° C., the $C_5$-hydrocarbons produced from TON are predominantly alkenes whereas the $C_5$-hydrocarbons produced from MFI are predominantly alkanes.

The performance of ZSM-23 and TON for olefin restructuring using a pure 1-butene feed are compared in Table 3. It is evident that the conversions and selectivities based on 1-butene are similar (Table 3 (a)). It is also evident that the $C_5$-hydrocarbons produced from reactions over ZSM-23 are predominantly alkenes, so are the $C_5$-hydrocarbons produced from reactions over TON (Table 3(b)).

The effect of reaction temperature for olefin restructuring using a dilute 1-butene feed for reactions over TON is shown in Table 4. It is also shown in Table 4 that TON can be calcined in air (in this case at 550° C.) to burn off carbonaceous residues thereby regenerating the zeolite without any deleterious effect on the performance of the catalyst for olefin restructuring.

The effect of space velocity for olefin restructuring on TON using a 1-butene feed is shown in Table 5. It is evident that the distribution of desired reaction products can be controlled by varying the space velocity. Thus at a lower space velocity (WHSV = 1.85 h$^{-1}$) the predominant products are $C_{5+}$ hydrocarbons which have previously been shown to be rich in alkenes. At higher space velocities (WHSV = 26.2 h$^{-1}$) the production of $C_{5+}$ hydrocarbons are smaller but the selectivity for isobutene production is higher.

The effect of time on stream upon olefin restructuring over TON is shown in Table 6. It is evident that at a reaction temperature of 379° C. using a diluted 1-butene feed, the selectivity for isobutene formation increases after 71 hours on stream whereas the selectivity for $C_{5+}$ hydrocarbon formation decreases.

Sample TON-C which was prepared using a diethanolamine template in the synthesis was also tested for olefin restructuring. The results of the tests using 1-butene as feed are shown in Table 7. It is evident that TON-C gives high selectivities for the formation of isobutene with a 10% 1-butene in nitrogen feed. For a pure 1-butene feed TON-C gives approximately equal selectivities for isobutene formation and $C_{5+}$ hydrocarbon formation, the latter of which is rich in alkenes. This test thus demonstrates that it can be beneficial to calcine tectometallosilicate prepared using an organic template at a low temperature e.g. 325° C.

TABLE 1

Olefin Restructuring Over MFI and TON: Comparative Test with Diluted-butene feed

Reaction Conditions (Table 1a, b and c)

| | |
|---|---|
| Feed: | 10.8 ± 0.5% v/v 1-butene in nitrogen |
| Catalyst: | MFI-B Si:Al:22:1 |
| | TON-B Si:Al:26:1 |
| Pressure | 100 kPa |
| Catalyst weight/g: | 0.5 g |
| WHSV (1-butene): | 7.2 ± 0.5 |
| Run time (mins): | between 30–42 |
| Catalyst pretreatment: | ammonium form of zeolites calcined at 400° C. in nitrogen for ca 14 hours. |

(a) Conversions and selectivities based on 1-butene fed

| Catalyst | Reaction Temp. °C. | 1-Butene Convn (mole %) | $C_{1-3}$ | $C_2=$ | $C_3=$ | $C_4$ | $2C_4=$ | $iC_4=$ | $C_{5+}$ |
|---|---|---|---|---|---|---|---|---|---|
| MFI-B (Comp Test) | 377 | 96.6 | 6.2 | 4.8 | 20.9 | 14.5 | 10.9 | 11.2 | 31.5 |
| TON-B | 379 | 90.0 | 0.9 | 0.8 | 10.6 | 3.8 | 33.7 | 35.0 | 15.2 |

(b) Conversions and selectivities based on n-butene fed

| Catalyst | Reaction Temp. °C. | n-Butene Convn (mole %) | $C_{1-3}$ | $C_2=$ | $C_3=$ | $C_4$ | $iC_4=$ | $C_{5+}$ |
|---|---|---|---|---|---|---|---|---|
| MFI-B (Comp Test) | 377 | 86.1 | 7.0 | 5.3 | 23.5 | 16.3 | 12.5 | 35.4 |
| TON-B | 379 | 59.7 | 1.3 | 1.2 | 15.9 | 5.7 | 52.9 | 22.9 |

(c) Composition of $C_5$-Hydrocarbons for Reactions in Table 1 (a, b)

| Catalyst | $C_5$-hydrocarbons (wt %) Alkanes | Alkenes |
|---|---|---|
| MFI-B | 34 | 66 |
| TON-B | 2 | 98 |

TABLE 2

Olefin Restructuring over TON and MFI: Comparative Test with pure 1-butene feed

Reaction Conditions (Table 2a and b)

| | |
|---|---|
| Feed: | 1-butene |
| Catalyst: | MFI-A Si:Al = 11.5:1 TON-B Si:Al = 26:1 |
| Pressure: | 100 kPa |
| Run time (mins): | 40 |
| WHSV | 6.6 ± 0.1 |
| Catalyst pretreatment: | Ammonium form of zeolites heated at 400° C. in nitrogen for ca 14 hours |

(a)

| Catalyst | Reaction Temp. °C. | 1-Butene Convn (mole %) | $2C_4=$ | $C_{1-4}$ not $C_4=$ | $iC_4=$ | $C_{5+}$ |
|---|---|---|---|---|---|---|
| MFI-A (Comp Test) | 273 | 99 | 3.5 | 7 | 3.5 | 86 |
| TON-B | 278 | 94.5 | 20 | 8 | 9 | 63 |

Composition of $C_5$-Hydrocarbons produced for reactions in Table 2(a)

| Catalyst | $C_5$-hydrocarbon composition (wt %) Alkanes | Alkenes |
|---|---|---|
| MFI-A (Comp Test) | 61 | 39 |
| TON-B | 12 | 88 |

TABLE 3

Olefin Restructuring over ZSM-23 and TON using a pure 1-butene feed

Reaction Conditions (Table 3a and b)

| | |
|---|---|
| Feed: | 1-butene |
| Zeolite: | ZSM-23 Si:Al::41:1, TON-B Si:Al::26:1 |
| Pressure: | 100 kPa |
| Catalyst weight/g: | 1.0 |
| Run time/min: | ZSM-23-(51), TON-(30) |
| WHSV: | 7.6 ± 0.1 |

TABLE 3-continued

Olefin Restructuring over
ZSM-23 and TON using a pure 1-butene feed

| Zeolite pretreatment: | Ammonium form of zeolite heated at 400° C. in nitrogen for approximately 14 hours. | | | | |
|---|---|---|---|---|---|
| (a) | | | | | |
| | Reaction Temp. | 1-Butene Convn | Selectivities based on 1-butene fed (mole %) | | |
| Catalyst | °C. | (mole %) | $C_{1-4}$ | $2C_4=$ | $iC_4=$ | $C_{5+}$ |
| ZSM-23 | 403 | 98.0 | 18.1 | 5.6 | 7.7 | 68.7 |
| TON-B | 387 | 98.4 | 15.0 | 4.3 | 5.1 | 75.6 |

(b) Composition of $C_5$-Hydrocarbons produced in reactions in Table 3a

| | $C_5$-hydrocarbon composition (% w/w) | |
|---|---|---|
| Catalyst | Alkanes | Alkenes |
| ZSM-23 | 8 | 92 |
| Theta-1 | 13 | 87 |

TABLE 4

Olefin Restructuring on TON:
Effect of Reaction Temperature and Regeneration

| Reaction Conditions (Table 4) | |
|---|---|
| Feed: | 11.5 ± 2.8% v/v 1-butene in nitrogen |
| Catalyst: | TON-A Si:Al::30:1 |
| Pressure: | 100 kPa |
| Catalyst weight/g: | 0.5 |
| Run time/min: | between 33–70 for each temperature |
| WHSV: | 7.6 to 9.0 |

| | 1-butene convn | Selectivity based on 1-butene (mole %) | | | |
|---|---|---|---|---|---|
| Temp/°C. | (mole %) | $C_{1-4}$ | $2C_4=$ | $iC_4=$ | $C_{5+}$ |
| 234 | 85.1 | 0 | 92.1 | 7.1 | 0.8 |
| 276 | 84.5 | 0.8 | 83.6 | 13.9 | 1.7 |
| 326 | 87.9 | 3.8 | 54.3 | 36.0 | 5.9 |
| 376 | 89.2 | 6.6 | 41.8 | 43.7 | 7.9 |
| Zeolite regenerated at 550° C./air/ca 16 hours | | | | | |
| 376 | 87.5 | 5.3 | 41.9 | 40.6 | 12.2 |
| 426 | 87.7 | 7.9 | 41.7 | 42.1 | 8.3 |
| 475 | 86.1 | 8.6 | 42.8 | 42.0 | 6.6 |

TABLE 5

Olefin Restructuring on TON: Effect of Space Velocity

| Reaction Conditions (Table 5) | |
|---|---|
| Feed: | 1-butene |
| Catalyst TON-B: | Si:Al::26:1 |
| Pressure: | 100 MPa |
| Catalyst weight: | Run A-2.0 g, Run B-1.0 g, Run C-0.5 g |
| Run time/min: | 30–41 |
| Catalyst pretreatment: | Ammonium form of zeolite calcined at 400° C. in nitrogen for approximately 14 hours |

| | | | 1-Butene | Selectivity (Mole %) based on 1-butene | | | | |
|---|---|---|---|---|---|---|---|---|
| Run | WHSV | Temperature °C. | Convn (mole %) | $C_{1-4}$ not $C_3=$ | $C_3=$ | $2C_4=$ | $iC_4=$ | $C_{5+}$ |
| A | 1.85 | 273 | 98.4 | 8.1 | 3.0 | 5.5 | 6.4 | 76.9 |
| B | 6.56 | 278 | 94.5 | 5.7 | 2.3 | 20.6 | 8.9 | 62.5 |
| C | 26.2 | 292 | 88.2 | 3.7 | 1.6 | 49.0 | 9.8 | 37.2 |

| Reaction Conditions (Table 6) | |
|---|---|
| Feed: | 12.1 ± 1.1% v/v 1-butene in nitrogen |
| Catalyst: | TON-B Si:Al::26:1 |
| Pressure: | 100 MPa |
| Catalyst weight/g: | 0.5 |
| Reaction temperature/°C. | 339 |
| WHSV (1-butene) | 7.9 ± 0.9 |
| Catalyst pretreatment: | Ammonium form of zeolite calcined at 400° C. in nitrogen for approximately 14 hours. Regenerated after previous reaction runs by calcining in air at 550° C. for about 14 hrs. |

TABLE 6

Olefin Restructuring on TON: Effect of Time on Stream

| | 1-Butene | Selectivity (Mole %) Based on 1-butene | | | | |
|---|---|---|---|---|---|---|
| Time on Stream/h | Convn (mole %) | $C_{1-4}$ not $C_4=$ or $C_3=$ | $C_3=$ | $2C_4=$ | $i-C_4=$ | $C_{5+}$ |
| 0.5 | 89.5 | 3.7 | 9.2 | 39.1 | 29.0 | 19.0 |
| 71 | 86.6 | 3.3 | 4.2 | 51.3 | 35.6 | 5.6 |

Olefin Restructuring over TON-C and TON-D using 1-butene feed : Effect of Low Temperature Calcination Catalyst Testing Both TON-C and TON-D were tested in a silica tubular reactor (internal diameter ca 10 mm) which was heated electrically. The feed used was 1-butene (99.9% w/w purity) at atmospheric pressure. The purity of both nitrogen when used as a diluent and air for calcination treatments was greater than 99% w/w. All the gases were dried before being fed to the reactor by passing the gases through traps containing calcium chloride and phosphorous pentoxide.

TABLE 7

Olefin Restructuring on TON: Effect of Modifications

Reaction Temperature: 400° C.
Pressure: 100 kPa
Run Duration: range of 2 to 20 hours

| Catalyst (2.0 g) | WHSV | Time of test period (hours) | n-Butene Conv. mole % | iso-$C_4=$ Yield mole % | Selectivities (based on n-butene) | | |
|---|---|---|---|---|---|---|---|
| | | | | | $C_{1-4}$ | $iC_4=$ | $C_5^+$ |
| TON-C calcined at 325° C. Feed: 100% 1-$C_4H_8$ | 13.0 | 5 | 53.0 | 25.5 | 9.8 | 48.1 | 42.1 |
| TON-C calcined at 500° C. Feed: 100% 1-$C_4H_8$ | 9.0 | 2 | 54.4 | 4.6 | 1.1 | 8.5 | 90.4 |
| TON-C calcined at 325° C. Feed: 50% 1-$C_4H_8$/50% $N_2$ | 5.0 | 2 | 51.3 | 29.9 | 10.3 | 58.3 | 31.4 |
| TON-C calcined at 325° C. Feed: 10% 1-$C_4H_8$/90% $N_2$ | 4.7 | 4 | 30.6 | 27.9 | 3.9 | 91.2 | 4.9 |
| TON-D calcined at 380° C. Feed: 50% 1-$C_4H_8$/50% $N_2$ | 9.5 | 3 | 51.6 | 37.5 | 11.4 | 72.7 | 15.9 |
| TON-D calcined at 360° C. Feed: 50% 1-$C_4H_8$/50% $N_2$ | 9.5 | 5 | 41.4 | 32.7 | 8.0 | 79.0 | 13.0 |
| TON-D calcined at 360° C. Feed: 100% 1-$C_4H_8$ | 19.0 | 6 | 39.9 | 28.9 | 10.0 | 72.4 | 17.5 |

We claim:

1. A process for isomerizing a $C_4$–$C_{10}$ olefinic feedstock rich in linear olefins comprising bringing the olefinic feedstock in the fluid phase into contact with a tectometallosilicate in its unmodified or partially modified H-form at an elevated temperature and, selecting obtaining a product having a higher proportion of corresponding branched chain olefins than the feedstock, the said tectometallosilicate in its calcined, organic free hydrogen form has the following composition in terms of the mole ratios of the oxides:

$$(0.9\pm0.1)H_{4-m}: XO_2: xSiO_2: yH_2O$$

wherein H is a proton, X is one or more of the metals selected from Al, Ga, Zn, Fe, Cr and B, m is the valency of the metal X in the metal oxide $XO_2$, x is at least 10, y/x is from 0 to 5 and the tectometallosilicate in its unmodified or partially modified H-form has an X-ray diffraction pattern as set forth in Table A (Theta-1) or Table B (ZSM-23) below:

TABLE A

| 2-theta (degrees) | d-spacing (Angstroms) | Relative Intensity 100 × $I/I_o$ |
|---|---|---|
| 8.06 ± 0.2 | 11.25–10.70 | 50 to 100 |
| 10.06 ± 0.2 | 9.01–8.63 | 5 to 30 |
| 12.69 ± 0.2 | 7.09–6.87 | 10 to 30 |
| 16.28 ± 0.2 | 5.51–5.38 | 5 to 15 |
| 19.40 ± 0.2 | 4.62–4.53 | 5 to 15 |
| 20.26 ± 0.2 | 4.43–4.34 | 50 to 100 |
| 24.11 ± 0.2 | 3.72–3.66 | 50 to 100 |
| 24.52 ± 0.2 | 3.66–3.60 | 30 to 90 |
| 25.65 ± 0.2 | 3.50–3.45 | 15 to 45 | scanned up to 2 theta = 32

TABLE B

| 2-theta (degrees) | d-spacing (Angstroms) | Relative Intensity 100 × $I/I_o$ |
|---|---|---|
| 7.94 ± 0.2 | 11.41–10.85 | 50 to 100 |

TABLE B-continued

| 2-theta (degrees) | d-spacing (Angstroms) | Relative Intensity 100 × $I/I_o$ |
|---|---|---|
| 8.24 ± 0.2 | 10.99–10.47 | 50 to 100 |
| 8.95 ± 0.2 | 10.10–9.66 | 20 to 50 |
| 11.44 ± 0.2 | 7.86–7.59 | 20 to 50 |
| 14.68 ± 0.2 | 6.11–5.95 | 5 to 10 |
| 15.90 ± 0.2 | 5.64–5.50 | 5 to 10 |
| 16.41 ± 0.2 | 5.75–5.39 | 5 to 10 |
| 18.28 ± 0.2 | 4.90–4.80 | 5 to 20 |
| 19.78 ± 0.2 | 4.53–4.44 | 50 to 100 |
| 20.16 ± 0.2 | 4.44–4.36 | 10 to 30 |
| 21.04 ± 0.2 | 4.26–4.18 | 50 to 100 |
| 22.98 ± 0.2 | 3.90–3.83 | 70 to 100 |
| 24.17 ± 0.2 | 3.71–3.65 | 50 to 100 |
| 24.82 ± 0.2 | 3.61–3.56 | 20 to 70 |
| 25.32 ± 0.2 | 3.54–3.49 | 20 to 60 |
| 26.15 ± 0.2 | 3.43–3.38 | 20 to 60 | scanned up to 2 theta = 32

2. A process according to claim 1 wherein the catalyst composition is subjected to an activation treatment thermochemically, which is heating in steam or in an atmosphere inert under the reaction conditions, either in an oxidative environment or in a reductive environment prior to contact with the olefinic feedstock.

3. A process according to claim 2 wherein the activation treatment is carried out in air or nitrogen at a temperature from 300°–600° C. and a pressure from 100–5000 KPa for 1 to 20 hours.

4. A process according to claim 1 wherein the olefinic feedstock is mixed with an inert diluent subjected to the reaction.

5. A process according to claim 4 wherein the diluent is nitrogen or a $C_1$–$C_{10}$ alkane.

6. A process according to claim 1 wherein the reaction is carried out at a temperature from 200°–550° C., a pressure from 100–1000 MPa and a WHSV of 1–100.

7. A process according to claim 4 wherein the restructuring reaction is carried out at a temperature from 200°–500° C.

8. A process according to claim 1 wherein the as synthesised tectometallosilicate is produced using ammonia as the template and partial modification of said as synthesised tectometallosilicate is carried out either as such or after conversion thereof to the H-form by stirring the tectometallosilicate in an organic compound at a temperature from 80°–120° C. followed by filtration, drying and calcination at a temperature from 200°–600° C.

9. A process according to claim 1 wherein the tectometallosilicate is bound in a binder prior to contact with the olefinic feedstock.

10. A process for isomerizing a $C_4$–$C_{10}$ olefinic feedstock rich in linear olefins comprising bringing the olefinic feedstock in the fluid phase into contact with a tectometallosilicate in its unmodified or partially modified H-form at an elevated temperature of from 200°–550° C. and selectively obtaining a product having a higher proportion of corresponding branched chain olefins than the feedstock, the said tectometallosilicate in its calcined, organic free hydrogen form has the following composition in terms of the mole ratios of the oxides:

$$(0.9 \pm 0.1)H_{4-m} : XO_2 : xSiO_2 : yH_2O$$

wherein H is a proton, X is one or more of the metals selected from Al, Ga, Zn, Fe, Cv, and B, m is the valency of the metal X in the metal oxide $XO_2$, x is at least 10, y/x is from 0 to 5 and the tectometallosilicate in its unmodified or partially modified H-form has an X-ray diffraction pattern substantially as set forth in Table A (Theta-1) below:

TABLE A

| 2-theta (degrees) | d-spacing (Angstroms) | Relative Intensity 100 × I/I$_o$ |
|---|---|---|
| 8.06 ± 0.2 | 11.25–10.70 | 50 to 100 |
| 10.06 ± 0.2 | 9.01–8.63 | 5 to 30 |
| 12.69 ± 0.2 | 7.09–6.87 | 10 to 30 |
| 16.28 ± 0.2 | 5.51–5.38 | 5 to 15 |
| 19.40 ± 0.2 | 4.62–4.53 | 5 to 15 |
| 20.26 ± 0.2 | 4.43–4.34 | 50 to 100 |
| 24.11 ± 0.2 | 3.72–3.66 | 50 to 100 |
| 24.52 ± 0.2 | 3.66–3.60 | 30 to 90 |
| 25.65 ± 0.2 | 3.50–3.45 | 15 to 45 | scanned up to 2 theta = 32.

* * * * *

UNITED STATES PATENT AND TRADEMARK OFFICE
CERTIFICATE OF CORRECTION

PATENT NO. : 5,434,328
DATED : July 18, 1995
INVENTOR(S) : SAMI A.I. BARRI, RABAAB TAHIR and DAVID W. WALKER It is certified that error appears in the above-indentified patent and that said Letters Patent is hereby corrected as shown below:

Col. 1, line 12, change "aluninosilicate" to --aluminosilicates--

Col. 2, lines 6 and 7, change "aluminosilicate" to --aluminosilicates--

Col. 6, lines 29 and 30, change "methanolamine" to --diethanolamine--

Column 15:
Claim 1, line 34 change "and, selecting" to --and selectively--

Column 16:
Claim 4, line 59 after "diluent" and before "subjected" insert --and--

Column 16:
Claim 6, line 65 change "MPa" to --KPa--

Column 16:
Claim 7, line 66 after "claim" change "4" to --6--

Signed and Sealed this

Twelfth Day of March, 1996

Attest:

BRUCE LEHMAN

*Attesting Officer*  *Commissioner of Patents and Trademarks*